United States Patent
Hunt

(10) Patent No.: US 8,632,785 B2
(45) Date of Patent: Jan. 21, 2014

(54) CLOSTRIDIAL TOXIN PHARMACEUTICAL COMPOSITION CONTAINING A GELATIN FRAGMENT

(75) Inventor: Terrence J. Hunt, Corona, CA (US)

(73) Assignee: Allergan, Inc., Irvine, CA (US)

(*) Notice: Subject to any disclaimer, the term of this patent is extended or adjusted under 35 U.S.C. 154(b) by 632 days.

(21) Appl. No.: 11/289,820

(22) Filed: Nov. 29, 2005

(65) Prior Publication Data

US 2006/0104994 A1    May 18, 2006

Related U.S. Application Data

(60) Continuation-in-part of application No. 10/976,371, filed on Oct. 29, 2004, which is a division of application No. 10/288,738, filed on Nov. 5, 2002, which is a continuation-in-part of application No. 10/047,058, filed on Jan. 14, 2002, now abandoned, which is a continuation-in-part of application No. 09/500,147, filed on Feb. 8, 2000, now abandoned.

(51) Int. Cl.
| A61K 39/08 | (2006.01) |
| A61K 38/17 | (2006.01) |
| C09H 3/00  | (2006.01) |
| C09H 3/02  | (2006.01) |

(52) U.S. Cl.
USPC .............. 424/247.1; 424/239.1; 530/354

(58) Field of Classification Search
None
See application file for complete search history.

(56) References Cited

U.S. PATENT DOCUMENTS

| 3,269,912 A | 8/1966 | Grafe |
| 3,758,382 A | 9/1973 | Knorpp |
| 4,016,354 A | 4/1977 | Greenwood |
| 4,029,765 A | 6/1977 | Helting |
| 4,391,801 A | 7/1983 | Ng et al. |
| 4,457,916 A | 7/1984 | Hayashi et al. ............... 424/101 |
| 4,578,270 A | 3/1986 | Csizer et al. |
| 4,597,966 A | 7/1986 | Zolton et al. |
| 4,613,500 A | 9/1986 | Suzuki et al. |
| 4,714,611 A | 12/1987 | Yasaburgo et al. |
| 4,904,467 A | 2/1990 | Schwulera |
| 4,962,091 A | 10/1990 | Eppstein et al. |
| 4,985,242 A | 1/1991 | Sekine et al. |
| 5,118,794 A | 6/1992 | Grangeorge et al. |
| 5,182,109 A | 1/1993 | Tamura et al. |
| 5,401,243 A | 3/1995 | Borodic |
| 5,437,291 A | 8/1995 | Pasricha et al. |
| 5,445,817 A | 8/1995 | Schneerson et al. |
| 5,466,672 A | 11/1995 | Kushnaryov et al. |
| 5,512,547 A | 4/1996 | Johnson et al. |
| 5,562,907 A | 10/1996 | Arnon |
| 5,609,871 A | 3/1997 | Michael et al. |
| 5,618,676 A | 4/1997 | Hitzeman et al. |
| 5,670,484 A | 9/1997 | Binder |
| 5,674,205 A | 10/1997 | Pasricha et al. |
| 5,695,956 A | 12/1997 | McClane et al. |
| 5,696,077 A * | 12/1997 | Johnson et al. ............... 514/2 |
| 5,698,536 A | 12/1997 | Segall et al. |
| 5,704,297 A | 1/1998 | Hussain et al. |
| 5,714,468 A | 2/1998 | Binder |
| 5,721,215 A | 2/1998 | Aoki et al. |
| 5,723,281 A | 3/1998 | Segall et al. |
| 5,730,969 A | 3/1998 | Hora et al. |
| 5,756,468 A | 5/1998 | Johnson et al. ............... 514/21 |
| 5,766,605 A | 6/1998 | Sanders et al. |
| 5,837,265 A | 11/1998 | Montal et al. |
| 5,846,929 A | 12/1998 | Johnson et al. |
| 5,905,143 A | 5/1999 | Johnson et al. |
| 5,908,825 A | 6/1999 | Fasano et al. |
| 5,919,463 A | 7/1999 | Thomas, Jr. et al. ........ 424/236.1 |
| 5,919,665 A | 7/1999 | Williams ............... 424/236.1 |
| 5,942,242 A | 8/1999 | Mizushima et al. ........ 424/236.1 |
| 5,945,098 A | 8/1999 | Sarno et al. |
| 5,997,856 A | 12/1999 | Hora et al. |
| 6,034,221 A | 3/2000 | Berezenko et al. |
| 6,051,239 A | 4/2000 | Simpson et al. |
| 6,087,327 A | 7/2000 | Pearce et al. ............... 514/2 |
| 6,113,915 A | 9/2000 | Aoki et al. |
| 6,139,845 A | 10/2000 | Donovan ............... 424/236.1 |
| 6,150,133 A | 11/2000 | Mead et al. |
| 6,238,664 B1 | 5/2001 | Hellerbrand et al. |
| 6,346,519 B1 | 2/2002 | Petrus |
| 6,358,917 B1 | 3/2002 | Carruthers et al. |
| 6,787,517 B1 | 9/2004 | Gil et al. |
| 6,992,172 B1 * | 1/2006 | Chang et al. ............... 530/354 |
| 7,211,261 B1 | 5/2007 | Moyer et al. |
| 8,137,677 B2 * | 3/2012 | Hunt ............... 424/234.1 |
| 8,216,591 B2 * | 7/2012 | Hunt ............... 424/247.1 |

(Continued)

FOREIGN PATENT DOCUMENTS

| CN | 1215084 | 4/1999 | ............ C12P 21/00 |
| EP | 0 123 291 | 10/1984 | |

(Continued)

OTHER PUBLICATIONS

Gartlan et al (Otolaryngo Head Neck Durg, 1993:108(2):135-140).*
Blair et al ( J. Clin. Neurosci 2004: 22(suppl1):S103-4 ABS-POS3R (Abstract only).*
Schantz et al (Microbiological Reviews, Mar. 1992,vol. 56, No. 1 p. 80-99).*
Olsen et al (Cambridge Healthtech Institute 's 2nd Annual International Transmissible Sponiform Encephalopathies (TSE Issue) in Alexandria, Virginia, Oct. 2-3, 2000).*
U.S. Appl. No. 09/500,147, filed Feb. 8, 2000, Hunt.
U.S. Appl. No. 10/047,058, filed Jan. 14, 2002, Hunt.
U.S. Appl. No. 10/288,738, filed Nov. 5, 2002, Hunt.
U.S. Appl. No. 10/976,371, filed Oct. 29, 2004, Hunt.

(Continued)

Primary Examiner — Nita M Minnifield
(74) Attorney, Agent, or Firm — Brigitte Phan; Ted Chan; Debra Condino

(57) ABSTRACT

A botulinum toxin pharmaceutical formulation comprising a botulinum toxin and a low molecular weight recombinant or native gelatin fragment suitable for administration to a human patient, and methods for treating patients with various diseases and afflictions using the formulation.

7 Claims, No Drawings

(56) References Cited

U.S. PATENT DOCUMENTS

| | | | |
|---|---|---|---|
| 8,323,666 B2* | 12/2012 | Hunt | 424/239.1 |
| 8,357,541 B2* | 1/2013 | Ton et al. | 436/161 |
| 8,501,196 B2* | 8/2013 | Hunt | 424/247.1 |
| 2002/0064536 A1 | 5/2002 | Hunt | 424/236.1 |
| 2003/0118598 A1 | 6/2003 | Hunt | 424/236.1 |
| 2003/0138437 A1 | 7/2003 | Hunt | 424/236.1 |
| 2005/0244358 A1 | 11/2005 | Ochoa | 424/70.13 |
| 2011/0152198 A1* | 6/2011 | Hunt | 514/18.8 |
| 2012/0141619 A1* | 6/2012 | Hunt | 424/780 |
| 2012/0237548 A1* | 9/2012 | Hunt | 424/239.1 |
| 2012/0238504 A1* | 9/2012 | Moyer et al. | 514/18.1 |
| 2012/0301455 A1* | 11/2012 | Hunt | 424/94.3 |

FOREIGN PATENT DOCUMENTS

| | | | |
|---|---|---|---|
| EP | 0150067 | 7/1985 | |
| EP | 0 330 451 | 8/1989 | |
| EP | 0361991 A2 | 4/1990 | |
| EP | 0 361 991 B1 | 12/1999 | |
| EP | 1 273 593 | 5/2002 | C07K 14/33 |
| WO | WO 90/03784 | 4/1990 | |
| WO | WO 96/03978 | 2/1996 | |
| WO | WO 96/11699 | 4/1996 | |
| WO | WO 96/37515 | 11/1996 | |
| WO | WO 97/35604 | 10/1997 | |
| WO | WO 00/15245 | * 3/2000 | |
| WO | WO 0015245 | * 3/2000 | |
| WO | WO 01/54711 | 1/2001 | A61K 38/16 |
| WO | WO 01/26736 | 4/2001 | A61K 38/16 |

OTHER PUBLICATIONS

Anderson and Harvey, Masticatory Muscle Myositis, *J. Vet. Dent.*, 1993, 10(1), pp. 6-8.
Annese, V., et al., Comparison of Two Different Formulations of Botulinum Toxin A for the Treatment of Oesophageal Achalasia, Ailment Pharmacol. Ther., 1999, 13, pp. 1347-1350.
Aoki K.R., *Pharmacology and immunology of botulinum toxin serotypes*, J Neurol 248(suppl 1);I/3-I/10:2001.
Aoki, R., *Preclinical update on BOTOX® (botulinum toxin type A)-purified neurotoxin complex relative to other botulinum neurotoxin preparations*, European Journal of Neurology, 1999, 6 (suppl 4):S3-S10.
Arnon, S.S., Clinical Botulism, chapter 13, pp. 145-150 of Brin M.F. et al, editors, *Scientific and therapeutic aspects of botulinum Toxin*, Lippincott, Williams & Wilkins (2002).
Bigalke, H., et al.; Factors Influencing Potency of Botulinum Toxin in Man; *Society for Neuroscience*, vol. 23 (1997); No. 870.10; p. 2234.
Binz T. et al., *The Complete Sequence of Botulinum Neurotoxin Type A and Comparison with Other Clostridial Neurotoxins*, J Biological Chemistry 265(16);9153-9158:1990.
Blair S., et al., *Skin sensitization potential of porcine gelatin, BOTOX(R) and BTXA in the guinea pig*, J Clin Neurosci 2004;22(Suppl 1):S103-4.
Bowen, *Am. J. Vet. Res.*, 35(5), 1974, pp. 661-668.
Brin, M.F., et al., Botulinum Toxin: Dangerous Terminology Errors, *Journal of the Royal Society of Medicine*, Aug. 1993, vol. 86, pp. 493-494.
British Pharmacopoeia 1999, *Hydroxyethylcellulose*, pp. 766-768.
Brochure: CALBIOCHEM®, Neurotoxin Type A, *Clostridium Botulinum*, Revised: Sep. 28, 1999.
Brochure: CALBIOCHEM®, Neurotoxin Type B, *Clostridium Botulinum*, Revised: Sep. 28, 1999.
Brochure: CALBIOCHEM®, Neurotoxin Type D, *Clostridium Botulinum*, Revised: Sep. 19, 2000.
Carpenter, J.F. et al., Interactions of Stabilizing Additives with Proteins During Freeze-Thawing and Freeze-Drying and Formulation, *International Symposium on Biological Product Freeze-Drying and Formulation*, Oct. 24-26, 1990, S. Karger AG (1992), pp. 225-239.
Carruthers, Alastair & Jean, Toxins 99, New Information About the Botulinum Neurotoxins, *Dermatol Surg*, 2000, 26(3), pp. 174-176.
Cohen and Thompson, Use of Botulinum Toxin to Lateralize True Vocal Cords: A Biochemical Method to Relieve Bilateral Abductor Vocal Cord Paralysis, *Ann. Otol. Rhinol. Laryngol.*, 96(5), 1987, pp. 534-541
Encinar et al., *FEBS Letters*, 429, 1998, p. 78.
European Pharmacopoeia 1999, *Hydroxyethylcellulose*, printed off CD ROM, pp. 1-7.
Farrugia C.A., et al, *Gelatin Denaturation and Renaturation Processes in Solution, Pharm. Res.* 14: S-160, 1997.
Gartlan, M.G., et al., Crystalline Preparation of Botulinum Toxin Type A (Botox): Degradation in Potency with Storage, *Otolaryngology—Head and Neck Surgery*, Feb. 1993, vol. 108, No. 2, pp. 135-140.
Gassner et al., *Plast. Reconstr. Surg.*, 105(6), 2000, pp. 1948-1955.
Gobel, H., et al., *Evidence-based medicine: botulinum toxin A in migraine and tension-type headache*, Journal of Neurology, 2001 248 Supp 1: I/34-I/38, XP-002182693.
Goodnough, M.C., et al., "Stabilization of Botulinum Toxin type A during Lyophilization" *Applied and Environmental Microbiology*, Oct. 1992, vol. 58, No. 10, p. 3426-3428.
Gui et al., Botulinum Toxin Injected in the Gastric Wall Reduces Body Weight and Food Intake in Rats, *Aliment Pharmacol Ther.*, 14(6), 2000, pp. 829-834.
Hawthorne et al., *J. Am. Anim. Hosp. Assoc.*, (1999) 35(2), pp. 135-146.
Heckmann, M., et al., *Botulinum Toxin A for Axilliary Hyperhidrosis (Excessive Sweating)*, N. Engl. J. Med., vol. 344, No. 7, Feb. 15, 2001, pp. 488-492.
Hickford et al., *J. Small Anim. Pract.*, 39(6), 1998, pp. 281-285.
Hoogerwerf, W.A. et al., Botulinum Toxin for Spastic Gastrointestinal Disorders, *Bailliere's Clinical Gastroenterology*, vol. 13, No. 1, 1999, pp. 135-146.
Horn et al., Botulinum Toxin Paralysis of the Orbicularis Oculi Muscle. Types and Tie Course of Alterations in Muscle Structure, Physiology and Lid Kinematics, *Exp. Brain Res.*, 96(1), 1993, pp. 534-541.
Inagi et al., Physiologic Assessment of Botulinum Toxin Effects in the Rat Larynx, *Laryngoscope*, 108(7), 1998, pp. 1048-1054.
Jost, W.H., *Ten Years' Experience with Botulin Toxin in Anal Fissure*, Internationa l Journal of Colorectal Disease (2002), 17; pp. 298-302.
Jurecka W., et al., *Hydroxyethylstarch deposits in human skin—a model for pruritus?*, Arch Dermatol Res. 1993;285(1-2):13-9.
Kobayashi, K. et al., The Development of Recombinant Human Serum Albumin, *Therapeutic Apheresis*, 1998, vol. 2, No. 4, pp. 257-262.
Kohl A., et al., *Comparison of the effect of botulinum toxin A (Botox (R)) with the highly-purified neurotoxin (NT 201) in the extensor digitorum brevis muscle test*, Mov Disord 2000;15 (Suppl 3):165.
Kohl, *Botulinum Toxin: Evidence-Based Medicine Criteria in Rare Indications*, J. Neurol., (2001), 248 (Suppl 1): 1/39-1/44.
Kondo H., et al, *Titration of botulinum toxins for lethal toxicity by intravenous injection into mice*, Jpn J Med Sci Biol 1984;37:131-5.
Label, 14/7683-006, Bayer Corporation, *Albumin (Human) 20%, USP Plasbumin-20*, May 1998.
Mahant, N., et al., *The Current Use of Botulinum Toxin*, Journal of Clinical Neuroscience, 7(5), 2000, pp. 389-394.
Marjama-Lyons, J. et al., Tremor-Predominant Parkinson's Disease, *Drugs & Aging*, Apr. 16, 2000(4), pp. 273-278.
Material Safety Data Sheet, Product #434965, Printed Aug. 9, 1999, 5 pages.
Melling, J. et al., Clostridium Botulinum Toxins: Nature and Preparation for Clinical Use; *Eye*, (1998) 2, pp. 16-23.
Naumann, M. et al., *Botulinum toxin type A in the treatment of focal, axillary and palmar hyperhidrosis and other hyperhidrotic conditions*, European Journal of Neurology 1999, 6 (suppl 4); S111-S115.
Ohtani, W., et al.; Physicochemical and Immunochemical Properties of Recombinant Human Serum Albumin from *Pichia pastoris; Analytical Biochemistry*; 1998; Article No. AB972480; No. 256; p. 56-62.
Olsen D., et al., Development of Recombinant Human Gelatins and Specific Molecular Type Human Gelatins, Oct. 2-3, 2000, *Cambridge Healthtech Institute's* 2nd Annual International Transmissible Spongiform Encephalopathies (TSE Issues), in Alexandria, Virginia.

(56) References Cited

OTHER PUBLICATIONS

Olsen D., et al., *Expression and characterization of a low molecular weight recombinant human gelatin: development of a substitute for animal derived gelatin with superior features*, J Protein Expression & Purification 40: 346-357 (2005).
Olsen D., et al., Expression and Characterization of Recombinant Human Gelatin Fragments, Oct. 29-Nov. 2, 2000, *American Association of Pharmaceutical Scientists (AAPS)* Annual Meeting and Exposition, Indianapolis, Indiana.
Olsen D., et al., *Recombinant collagen and gelatin for drug delivery*, Adv Drug Deliv Rev. Nov. 28, 2003;55(12):1547-67.
Olsen R., et al., Development of Recombinant Human Gelatin for Use as a Stabilizer in Biopharmaceuticals, Sep. 22-24, 2003, *Formulation Strategies for Biopharmaceuticals*, Philadelphia, PA.
Package Insert Y36-002-345; DuPont Pharma, HESPAN®, 2 pages.
Parth E., et al., *Histological and immunohistochemical investigations of hydroxyethyl-starch deposits in rat tissues*, Eur Surg Res. 1992;24(1):13-21.
Peters, T., Jr., et al., Practical Aspects: Albumin in the Laboratory, *All About Albumin Biochemistry, Genetics and Medical Applications*, Academic Press (1996), Chapter 7, pp. 295 & 298-305.
Porta, M., et al., *The Rationale and Results of Treating Muscle Spasm and Myofascial Syndromes with Botulinum Toxin Type A*, Pain Digest, 8(6), 1998, pp. 346-352.
Porter, C.J.H., Drug Delivery to the Lymphatic System, *Critical Reviews™ in Therapeutic Drug Carrier Systems*, 1997, 14(4), pp. 333-393.
Rader R.A., *Botulinum toxin A*, in Ronald Rader, ed. *BIOPHARMA: Biopharmaceutical Products in the U.S. Market* Rockville, MD: Biotechnology Information Institute; 2001:pp. 271-274 (332).
Rader R.A., *Botulinum toxin B*, in Ronald Rader, ed. *BIOPHARMA: Biopharmaceutical Products in the U.S. Market* Rockville, MD: Biotechnology Information Institute; 2001:pp. 274-276 (333).
Ragona, R.M., et al., *Management of Parotid Sialocele with Botulinum Toxin*, The Laryngoscope, Aug 109(8); 1999, pp. 1344-1346.
Reichel, G., *Botulinum Toxin for Treatment of Spasticity in Adults*, J. Neurol, 248 (Suppl. 1): 1/25-1/27 (2001).
Reimann S., et al., [*Hydroxyethyl starch accumulation in the skin with special reference to hydroxyethyl starch-associated pruritus*]; Dtsch Med Wochenschr. Mar. 10, 2000;125(10):280-5.
Rollnik, J.D., et al., "Low-dose treatment of cervical dystonia, blepharospasm and facial hemispasm with albumin-diluted botulinum toxin type A under EMG Guidance" *Eur Neurol* 2000;43:9-12.
Salioloa, M. et al., Use of the KIADH4 Promoter for Ethanol-Dependent Production of Recombinant Human Serum Albumin in *Kluyveromyces lactis, Appl. Environ. Microbiol.*, Jan. 1999, vol. 65, No. 1, pp. 53-60.
Schantz, E., et al., Preparation and characterization of botulinum toxin type A for human treatment, chapter 3 In: Jankovic J, ed. *Neurological Disease and Therapy. Therapy with Botulinum Toxin*, New York: Marcel Dekker;1994, pp. 41-49.
Schantz, E.J. et al., Properties and Use of Botulinum Toxin and Other Microbial Neurotoxins in Medicine, *Microbiological Reviews*, Mar. 1992, vol. 56, No. 1, pp. 80-99.
Schantz, E.J. et al., Standardized Assay for Clostridium Toxins, *Journal of the AOAC*, 1978, vol. 61, No. 1, pp. 96-99.
Schantz, E.J. et al., Use of Crystalline Type A Botulinum Toxin in Medical Research, *Biomedical Aspects of Botulism*, Academic Press (1981), pp. 143-150.
Schmidt, J.J. et al., Endoproteinase Activity of Type A Botulinum Toxin in Medical Research: Substrate Requirements and Activation by Serum Albumin, *Journal of Protein Chemistry*, 1997, vol. 16, No. 1, pp. 19-26.
Sheridan, R., *Comparison of In Vivo and In Vitro Mouse Bioassays for Botulinum Toxin Antagonists*, Journal of Applied Toxicology, (1999), 19, S29-S33.
Sigma 1999 Catalog, *Biochemicals and Reagents for Life Science Research*, pp. 187, 188 and 237.

Silberstein, S., et al., *Botulinum toxin type A as a migraine preventive treatment*, Headache 2000:40:445-450, XP-002182692.
Simpson, D., *Treatment of Spasticity with Botulinum Toxin*, Muscle & Nerve, Apr. 2000, pp. 447-449.
Singh, B.R., Critical Aspects of Bacterial Protein Toxins, *Natural Toxins II*, 1996, edited by B.R. Singh et al., Plenum Press, New York, Chapter 4, pp. 63-84.
Sirtl, C., et al., *Tissue deposits of hydroxyethyl starch (HES): dose-dependent and time-related*, Br J Anaesth. Apr. 1999;82(4):510-5.
Sloop, Richard R. et al., Reconstituted botulinum toxin type A does not lose potency in humans if it is refrozen or refrigerated for 2 weeks before use, *Neurology*, 48, Jan. 1997, pp. 249-253.
Storr and Allescher, *Esophageal Pharmacology and Treatment of Primary Motility Disorders*, Diseases of the Esophagus, 1999, 12, pp. 241-257.
Summary Basis of Approval (Apr. 12, 1999), OB-NDA 20/0952, 4 pages.
Tsuda, M., et al.; In vivo Pathway of Thermal Hyperalgesia by Intrathecal Administration of α,β-methylene ATP in Mouse Spinal Cord: Involvement of the Glutamate-NMDA Receptor System; *Br. J. Pharmacol* (1999); 127(2):449-456.
USP 23-NF 18, Supp. 10, *Hydroxyethyl Cellulose*, printed off CD ROM, p. 1-2.
Wohlfarth, H. et al., Effect for Dilution on Activity of Commercial Preparations of Botulinum Toxin A in Man, *Society for Neuroscience*, vol. 23 (1997), No. 870.11, p. 2234.
Yang C., et al, *Development of a recombinant human collagen-type III based hemostat*, J Biomed Mater Res. Apr. 15, 2004;69B(1), pp. 18-24.
Yang C., et al., *The application of recombinant human collagen in tissue engineering*, BioDrugs. 2004;18(2), pp. 103-119.
Yoneda, Shinji, et al., *Comparison of the therapeutic indexes of different molecular forms of botulinum toxin type A*, European Journal of Pharmacology, 508 (2005), pp. 223-229.
Ballance, et al., *Yeast-derived recombinant human albumin (Recombumin)*, Anasthesiol Intensivmed Notfallmd Schmerzther, 1999; 34(12):775-777.
Banga, *Therapeutic Peptides and Proteins: Formulation, Processing and Delivery Systems*, $2^{nd}$ Edition, CRC Press, Boca Raton, FL, pp. 108-110, 1995.
Begg, G.E. and David W. Speicher, *Mass Spectrometry Detection and Reduction of Disulfide Adducts Between Reducing Agents and Recombinant Proteins With Highly Reactive Cysteines*, Journal of Biomolecular Techniques, 1999; 10(1):17-20.
Biesman, et al., Ophthalmology Times, Apr. 1, 1997; 13-15.
Bigalke, H., et al., *Blockade by Tetanus and Botulinum A Toxin of Postganglionic Cholinergic Nerve Endings in the Myenteric Plexus*, Nauyn-Schmiedeberg's Archives of Pharmacology 312, 255-263 (1980).
BioTime, Inc, Summary Basis of Approval, Apr. 12, 1999.
Boldyrev, International Journal of Biochemistry, 1990; 22(2):129-132.
Botox Label and Approval History for Botox Cosmetic BLA No. 103000, Approved Apr. 12, 2000, www.accessdata.fda.gov/scripts/cder/drugsatfda/index.cfm?fuseaction=Search.Label_Approval History, printed Jan. 27, 2006.
Botox Product Information Sheet, http://www.botoxcosmetic.com/resources.pi.aspx., accessed on Jul. 5, 2007.
Brewster et al., *The Potential Use of Cyclodextrins in Parenteral Formulations*, J Parenter Sci Technol. Sep.-Oct. 1989;43(5):231-40.
Budsberg, et al., AJVR, Dec. 1996; 57(12).
Chuang, et al., *Pharmaceutical Strategies Utilizing Recombinant Human Serum Albumin*, Pharmaceutical Research, May 2002; 19(5):569-577.
Creighton, Thomas E., *Protein Structure: A Practical Approach*, 1989; 184-186.
Creighton, Thomas E., *Proteins: Structures and Molecular Properties*, 1984; 314-315.
Dodsworth, et al., *Comparative studies of recombinant human albumin and human serum albumin derived by blood fractionation*, Biotechnology and Applied Biochemistry, 1996; 24(2):171-176.
Gibson, Jr., et al., International Journal of Pediatric Otorhinolaryngology, Jan. 1994; 28(2-3):Abstract only.

(56) References Cited

OTHER PUBLICATIONS

Giebink, Vaccine, 2001; 19:S129-S133.

Hankins, et al., Dermatologic Surgery, 1998; 24:1181-1183.

Harlow, et al., *Antibodies A Laboratory Manual*, 1998; 66-67.

Hermeling, S., et al., *Antibody response to aggregated human interferon alpha2b in wild-type and transgenic immune tolerant mice depends on type and level of aggregation*, Journal of Pharmaceutical Sciences, May 2006; 95(5):1084-1096.

Jankovic, J. et al., *Therapeutic Uses of Botulinum Toxin*, New England Journal of Medicine, Apr. 25, 1991;324(17):1186-94.

Jameel, F. et al., PDA Journal of Pharmaceutical Science & Technology, 39(3): 127-131 (May-Jun. 1995).

Kaplan and Pesce, *Clinical Chemistry, Theory, Analysis and Correlation*, The C.V. Mosby Company, 1984; 924-926.

Khawaja, et al., International Journal of Dermatology, May 2001; 40:311-317.

McLellan, et al., Toxicon, 1996; 34(9):975-985.

McNally, *Protein Formulation and Delivery*, Marcel Dekker, Inc., New York, p. 145, 2000.

Meltzer, et al., Journal of Allergy and Clinical Immunology, 2000; 106(4).

Nosoh, Y., et al., *Protein Stability and Stabilization through Protein Engineering*, 1991; 197.

Ohtani, et al., *Structure of recombinant human serum albumin from Pichia pastoris*, Yakugaku Zasshi, 1997; 117(12):1033.

Patten, P.A., et al., *The immunogenicity of biopharmaceuticals. Lessons learned and consequences for protein drug development*, Journal of Developmental Biology (Basel), 2003; 112:81-97.

Pearce, et al., Toxicon, 1995; 33:217-227.

Pearce, et al., Journal of the Royal Society of Medicine, 1995; 88:239-240.

Polysaccharides, Article from de.wikipedia.org, printed Jan. 26, 2006.

Sesardic, et al., Biologicals, 2003; 31:265-276.

Szokoloczy, Magyar Allatorvosok Lapja, 1980; 35(6):423-426.

Tabita, et al., Jpn J Med Sci Biol, 1990; 43:219-231.

Tarelli, et al., *Recombinant human albumin as a stabilizer for biological materials and for the preparation of international reference reagents*, Biologicals, 1998; 26(4):331-346.

Zhang, et al., Gene, 2003; 315:21-32.

\* cited by examiner

CLOSTRIDIAL TOXIN PHARMACEUTICAL COMPOSITION CONTAINING A GELATIN FRAGMENT

CROSS REFERENCE

This application is a continuation in part of application Ser. No. 10/976,371, filed Oct. 29, 2004, which is a divisional of application Ser. No. 10/288,738, filed Nov. 5, 2002, which is a continuation in part of application Ser. No. 10/047,058, filed Jan. 14, 2002, now abandoned, which is a continuation in part of application Ser. No. 09/500,147, filed Feb. 8, 2000, now abandoned. The entire contents of these prior patent applications are incorporated herein by reference.

BACKGROUND

The present invention relates to Clostridial toxin pharmaceutical compositions containing one or more gelatin fragments. In particular, the present invention relates to botulinum toxin pharmaceutical compositions stabilized with one or more gelatin fragments and uses thereof. The gelatin fragments can be made by a recombinant process or can be obtained by separation of particular desired gelatin fragments obtained from digestion or degradation of a larger gelatin molecule made by native or natural cellular processes.

A pharmaceutical composition is a formulation which contains at least one active agent or active pharmaceutical ingredient ("API"), such as a Clostridial toxin, such as a botulinum neurotoxin. In addition to an API a pharmaceutical composition also contains one or more excipients, buffers, carriers, stabilizers, preservatives and/or bulking agents. A pharmaceutical composition is suitable for administration to a human patient to achieve a desired diagnostic, therapeutic or cosmetic result.

For storage stability and convenience of handling, a pharmaceutical composition can be formulated as a lyophilized (i.e. freeze dried) or vacuum dried powder. For administration as a aqueous solution the lyophilized or vacuum dried powder pharmaceutical composition is reconstituted with a suitable fluid, such as saline or water, prior to administration to a patient. Alternately, a pharmaceutical composition can be formulated as an aqueous solution or suspension, or as a cream, gel, emollient, depot, implant or the like. A pharmaceutical composition can contain a proteinaceous active ingredient. Unfortunately, a protein active ingredient can be very difficult to stabilize (i.e. maintained in a state where loss of biological activity is minimized), resulting therefore in a loss of protein and/or loss of protein activity during the formulation, reconstitution (if required) and during the period of storage prior to use of a protein containing pharmaceutical composition. Stability problems can occur because of protein active ingredient denaturation, degradation, dimerization, and/or polymerization. Various excipients or bulking agents, such albumin, gelatin, dextran, sucrose, etc, have been used with differing degrees of success to try and stabilize a protein active ingredient present in a pharmaceutical composition. Additionally, cryoprotectants such as alcohols have been used to reduce protein denaturation under the freezing conditions of lyophilization.

Gelatin

Collagen is the most abundant protein in mammals comprising about one quarter of all protein in the body and it is the major constituent of connective tissues, such as skin, ligaments and tendons. Native collagen is a triple helix of three high molecular weight proteins. Each of the three protein chains comprising the collagen helix has more than 1400 amino acids. At least twenty five distinct types of collagens have been identified in humans.

Gelatin can be obtained from natural sources by hydrolysis of collagen. A hydrolysate of collagen is a hetergenous mixture of hundreds of different size peptides. Thus, native gelatin comprises numerous denatured collagen protein fragments. Hydrolysates of collagen (i.e. gelatin) have been used to stabize various vacines, including vaccines directed to measles, influenza, mumps, varicella and rubella, rabies, diptheria, tetanus and pertussis. Since the gelatin USP used in pharmaceutical preparations is a mixture of protein molecules derived from hydrolysis of animal collagen the molecular weight of the numerous various gelatin molecules present in gelatin USP (a collagen hydrolysate) can vary from less than about 50 kDa to greater than about 1800 kDa. Farrugia C. A., et al, *Gelatin Denaturation and Renaturation Processes in Solution*, Pharm. Res. 14: S-160, 1997.

It is know to make and use recombinant collagens and gelatins. See e.g. Yang C., et al, *Development of a recombinant human collagen-type III based hemostat*, J Biomed Mater Res. Apr. 15, 2004;69B(1):18-24, and Yang C., et al., *The application of recombinant human collagen in tissue engineering*, BioDrugs. 2004; 18(2):103-19.

Additionally, use of recombinant collagens and gelatins in drug delivery has been proposed. See e.g. Olsen D., et al., *Recombinant collagen and gelatin for drug delivery*, Adv Drug Deliv Rev. Nov. 28, 2003;55(12):1547-67; Olsen R., et al., *Development of Recombinant Human Gelatin for Use as a Stabilizer in Biopharmaceuticals*, Sep. 22-24, 2003, Formulation Strategies for Biopharmaceuticals, Philadelphia, Pa.;Olsen D., et al., *Development of Recombinant Human Gelatins and Specific Molecular Type Human Gelatins*, Oct. 2-3, 2000, Cambridge Healthtech Institute's 2nd Annual International Transmissible Spongiform Encephalopathies (TSE Issues), in Alexandria, Virginia, and; Olsen D., et al., *Expression and Characterization of Recombinant Human Gelatin Fragments*, October 29-Nov. 2, 2000, American Association of Pharmaceutical Scientists (AAPS) Annual Meeting and Exposition, Indianapolis, Ind.

Furthermore, recombinant expression of gelatin fragments has been reported. Olsen D., et al., *Expression and characterization of a low molecular weight recombinant human gelatin: development of a substitute for animal derived gelatin with superior features*, J Protein Expression & Purification 40: 346-357 (2005).

Native gelatin has been used as an excipient in a botulinum toxin formulation (see eg Chinese patent CN 1215084A). Significantly, it is known that gelatin used in such a pharmaceutical preparation can cause an immunologic reaction. Blair S., et al., *Skin sensitization potential of porcine gelatin, BOTOX® and BTXA in the guinea pig*, J Clin Neurosci 2004; 22(Suppl 1):S103-4.

Thus, significant drawbacks such as immunogenicity exist from use of gelatin (for example as a collagen hydrolysate) in a pharmaceutical composition. Additionally, gelatin is expensive and increasingly difficult to obtain. Furthermore as an animal derived protein, when incorporated into a pharmaceutical composition gelatin can present a risk of transmitting one or more pathogens or infectious agents such as prions. A prion is a proteinaceous infectious particle which is hypothesized to arise as an abnormal conformational isoform from the same nucleic acid sequence which makes the normal protein. Infectivity of a prion may reside in a "recruitment reaction" of the normal isoform protein to the prion protein isoform at a post translational level. Apparently the normal endogenous cellular protein is induced to misfold into a pathogenic prion conformation.

Botulinum Toxin

The anaerobic, gram positive bacterium *Clostridium botulinum* produces a potent polypeptide neurotoxin, botulinum toxin, which causes a neuroparalytic illness in humans and animals referred to as botulism. *Clostridium botulinum* and its spores are commonly found in soil and the bacterium can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of botulinum toxin (purified neurotoxin complex) type A is a $LD_{50}$ in mice. Interestingly, on a molar basis, botulinum toxin type A is 1.8 billion times more lethal than diphtheria, 600 million times more lethal than sodium cyanide, 30 million 10 times more lethal than cobrotoxin and 12 million times more lethal than cholera. Singh, *Critical Aspects of Bacterial Protein Toxins*, pages 63-84 (chapter 4) of Natural Toxins II, edited by B. R. Singh et al., Plenum Press, New York (1976) (where the stated $LD_{50}$ of botulinum toxin type A of 0.3 ng equals 1 U is corrected for the fact that about 0.05 ng of BOTOX®) equals 1 unit). One unit (U) of botulinum toxin is defined as the $LD_{50}$ upon intraperitoneal injection into female Swiss Webster mice weighing 18-20 grams each. In other words, one unit of botulinum toxin is the amount of botulinum toxin that kills 50% of a group of female Swiss Webster mice. Seven generally immunologically distinct botulinum neurotoxins have been characterized, these being respectively botulinum neurotoxin serotypes A, B, $C_1$, D, E, F, and G, each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. The botulinum toxins apparently bind with high affinity to cholinergic motor neurons, are translocated into the neuron and block the presynaptic release of acetylcholine.

Botulinum toxins have been used in clinical settings for the treatment of neuromuscular disorders characterized by hyperactive skeletal muscles. Botulinum toxin type A was approved by the U.S. Food and Drug Administration in 1989 for the treatment of essential blepharospasm, strabismus and hemifacial spasm in patients over the age of twelve. Clinical effects of peripheral injection (i.e. intramuscular or subcutaneous) botulinum toxin type A are usually seen within one week of injection, and often within a few hours after injection. The typical duration of symptomatic relief (i.e. flaccid muscle paralysis) from a single intramuscular injection of botulinum toxin type A can be about three months to about six months.

Although all the botulinum toxins serotypes apparently inhibit release of the neurotransmitter acetylcholine at the neuromuscular junction, they do so by affecting different neurosecretory proteins and/or cleaving these proteins at different sites. Botulinum toxin A is a zinc endopeptidase which can specifically hydrolyze a peptide linkage of the intracellular, vesicle associated protein SNAP-25. Botulinum type E also cleaves the 25 kiloDalton (kD) synaptosomal associated protein (SNAP-25), but targets different amino acid sequences within this protein, as compared to botulinum toxin type A. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain (H chain) and a cell surface receptor; the receptor is thought to be different for each serotype of botulinum toxin and for tetanus toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This last step is thought to be mediated by the amino end segment of the H chain, $H_N$, which triggers a conformational change of the toxin in response to a pH of about 5.5 or lower. Endosomes are known to possess a proton pump which decreases intra endosomal pH. The conformational shift exposes hydrophobic residues in the toxin, which permits the toxin to embed itself in the endosomal membrane. The toxin then translocates through the endosomal membrane into the cytosol.

The last step of the mechanism of botulinum toxin activity appears to involve reduction of the disulfide bond joining the H and L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin B, D, F, and G cause degradation of synaptobrevin (also called vesicle-associated membrane protein (VAMP)), a synaptosomal membrane protein. Most of the VAMP present at the cytosolic surface of the synaptic vesicle is removed as a result of any one of these cleavage events. Each toxin specifically cleaves a different bond.

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and $C_1$ are apparently produced as only a 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemagglutinin protein and a non-toxin and non-toxic nonhemagglutinin protein. These two non-toxin proteins (which along with the botulinum toxin molecule can comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex. The toxin complexes can be dissociated into toxin protein and hemagglutinin proteins by treating the complex with red blood cells at pH 7.3. The toxin protein has a marked instability upon removal of the hemagglutinin protein.

All the botulinum toxin serotypes are made by *Clostridium botulinum* bacteria as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D, and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, CGRP and glutamate.

High quality crystalline botulinum toxin type A can be produced from the Hall A strain of *Clostridium botulinum* with characteristics of $\geq 3 \times 10^7$ U/mg, an $A_{260}/A_{278}$ of less than 0.60 and a distinct pattern of banding on gel electrophoresis. The known Schantz process can be used to obtain crystalline botulinum toxin type A, as set forth in Schantz, E. J., et al, *Properties and use of Botulinum toxin and Other Microbial Neurotoxins in Medicine*, Microbiol Rev. 56: 80-99 (1992). Generally, the botulinum toxin type A complex can be isolated and purified from an anaerobic fermentation by cultivating *Clostridium botulinum* type A in a suitable medium. Raw toxin can be harvested by precipitation with sulfuric acid and concentrated by ultramicrofiltration. Purification can be carried out by dissolving the acid precipitate in calcium chloride. The toxin can then be precipitated with cold ethanol. The precipitate can be dissolved in sodium phosphate buffer and centrifuged. Upon drying there can then be obtained approximately 900 kD crystalline botulinum toxin type A complex with a specific potency of $3 \times 10^7$ $LD_{50}$ U/mg or greater. This known process can also be used, upon separation out of the non-toxin proteins, to obtain pure botulinum toxins, such as for example: purified botulinum toxin type A with an approximately 150 kD molecular weight with a specific potency of $1-2 \times 10^8$ $LD_{50}$ U/mg or greater; purified botulinum toxin type B with an approximately 156 kD molecular weight with a specific potency of $1-2 \times 10^8$ $LD_{50}$ U/mg or greater, and; purified botulinum toxin type F with an approximately 155 kD molecular weight with a specific potency of $1-2 \times 10^7$ $LD_{50}$ U/mg or greater.

Already prepared and purified botulinum toxins and toxin complexes suitable for preparing pharmaceutical formulations can be obtained from List Biological Laboratories, Inc., Campbell, Calif.; the Centre for Applied Microbiology and Research, Porton Down, U.K.; Wako (Osaka, Japan), as well as from Sigma Chemicals of St Louis, Mo.

It has been reported that BoNt/A has been used in clinical settings as follows:

(1) about 75-125 units of BOTOX®[1] per intramuscular injection (multiple muscles) to treat cervical dystonia;

[1] Available from Allergan, Inc., of Irvine, Calif. under the tradename BOTOX®.

(2) 5-10 units of BOTOX® per intramuscular injection to treat glabellar lines (brow furrows) (5 units injected intramuscularly into the procerus muscle and 10 units injected intramuscularly into each corrugator supercilli muscle);

(3) about 30-80 units of BOTOX® to treat constipation by intrasphincter injection of the puborectalis muscle;

(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:

(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

Additionally, intramuscular botulinum toxin has been used in the treatment of tremor in patients with Parkinson's disease, although it has been reported that results have not been impressive. Marjama-Lyons, J., et al., *Tremor-Predominant Parkinson's Disease*, Drugs & Aging 16(4);273-278:2000.

It is known that botulinum toxin type A can have an efficacy for up to 12 months (*European J. Neurology* 6 (8upp 4): 8111-81150:1999), and in some circumstances for as long as 27 months. *The Laryngoscope* 109:1344-1346:1999. However, the usual duration of an intramuscular injection of BOTOX® is typically about 3 to 4 months.

The success of botulinum toxin type A to treat a variety of clinical conditions has led to interest in other botulinum toxin serotypes. Additionally, pure botulinum toxin has been used in humans. see e.g. Kohl A., et al., *Comparison of the effect of botulinum toxin A (Botox (R)) with the highly-purified neurotoxin (NT201) in the extensor digitorum brevis muscle test*, Mov Disord 2000;15(Suppl 3):165 Hence, a pharmaceutical composition can be prepared using a pure botulinum toxin.

The botulinum toxin molecule (about 150 kDa), as well as the botulinum toxin complexes (about 300-900 kDa), such as the toxin type A complex are also extremely susceptible to denaturation due to surface denaturation, heat, and alkaline conditions. Inactivated toxin forms toxoid proteins which may be immunogenic. The resulting antibodies can render a patient refractory to toxin injection.

As with enzymes generally, the biological activities of the botulinum toxins (which are intracellular peptidases) are dependant, at least in part, upon their three dimensional conformation. Thus, botulinum toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin must be stabilized with a stabilizing agent. To date, the only successful stabilizing agent for this purpose has been the animal derived proteins human serum albumin and gelatin. And as indicated, the presence of animal derived proteins in the final formulation presents potential problems in that certain stable viruses, prions, or other infectious or pathogenic compounds carried through from donors can contaminate the toxin.

Furthermore, any one of the harsh pH, temperature and concentration range conditions required to lyophilize (freeze-dry) or vacuum dry a botulinum toxin containing pharmaceutical composition into a toxin shipping and storage format (ready for use or reconstitution by a physician) can detoxify the toxin. Thus, animal derived or donor pool proteins such as gelatin and serum albumin have been used with some success to stabilize botulinum toxin.

A commercially available botulinum toxin containing pharmaceutical composition is sold under the trademark BOTOX® (available from Allergan, Inc., of Irvine, Calif.). BOTOX® consists of a purified botulinum toxin type A complex, human serum albumin, and sodium chloride packaged in sterile, vacuum-dried form. The botulinum toxin type A is made from a culture of the Hall strain of *Clostridium botulinum* grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. BOTOX® can be reconstituted with sterile, non-preserved saline prior to intramuscular injection. Each vial of BOTOX® contains about 100 units (U) of *Clostridium botulinum* toxin type A complex, 0.5 milligrams of human serum albumin and 0.9 milligrams of sodium chloride in a sterile, vacuum-dried form without a preservative.

To reconstitute vacuum-dried BOTOX® sterile normal saline without a preservative (0.9% Sodium Chloride injection) is used by drawing up the proper amount of diluent in the appropriate size syringe. Since BOTOX® is denatured by bubbling or similar violent agitation, the diluent is gently injected into the vial. For sterility reasons, BOTOX® should be administered within four hours after reconstitution. During this time period, reconstituted BOTOX® is stored in a refrigerator (2° to 8° C.). Reconstituted BOTOX® is clear, colorless and free of particulate matter. The vacuum-dried product is stored in a freezer at or below −5° C.

Other commercially available botulinum toxin containing pharmaceutical compositions include DYSPORT® (Clostridium botulinum type A toxin hemagglutinin complex with human serum albumin and lactose in the formulation, available from Ipsen Limited, Berkshire, U.K. as a powder to be reconstituted with 0.9% sodium chloride before use), and MYOBLOC™ (an injectable solution comprising botulinum toxin type B, human serum albumin, sodium succinate, and sodium chloride at about pH 5.6, available from Elan Corporation, Dublin, Ireland).

Chinese patent CN 1215084 discusses an albumin free botulinum toxin type A formulated with native gelatin (a collagen hydrolysate), an animal derived protein, dextran and sucrose. U.S. Pat. No. 6,087,327 also discloses a composition of botulinum toxin types A and B formulated with native gelatin.

What is needed therefore is a botulinum toxin containing pharmaceutical composition in which the botulinum toxin present in the pharmaceutical composition is stabilized (i.e. has a high recovered potency) by one or more protein fragments present in the pharmaceutical composition, such as a protein fragment (such as a gelatin fragment) made by a recombinant process or obtained by the digestion or degradation of a larger protein made by a native or natural cellular processes. Preferably, the protein fragment is not an animal derived protein such as a native gelatin and/or is not a mixture of numerous (i.e. hundreds) of different gelatin fragments.

SUMMARY

The present invention meets this need and provides a botulinum toxin pharmaceutical composition in which the botulinum toxin present in the pharmaceutical composition is stabilized (i.e. has a high recovered potency) by one or more protein fragments present in the pharmaceutical composition. The protein fragment can be made recombinantly or obtained by the digestion or degradation of a larger protein made by a native or natural cellular processes. Preferably, the protein fragment is not an animal derived protein such as a native gelatin.

The present invention encompasses new pharmaceutical compositions, embodiments of which can provide a superior replacement (i.e. by use of a recombinant gelatin fragment, with or without additional stabilizers) for the serum or native albumin or native gelatin present as a primary stabilizer in a pharmaceutical composition. Thus, my invention encompasses new, stabilized botulinum toxin pharmaceutical compositions with the desirable characteristic of a high recovered potency. The protein fragment used has the characteristic of low, and preferably negligible, immunogenicity when injected into a patient. Additionally, the preferred protein fragment can have a rapid rate of clearance from the body after injection of a botulinum toxin pharmaceutical composition containing the protein fragment.

Definitions

As used herein, the words or terms set forth below have the following definitions.

"About" means that the item, parameter or term so qualified encompasses a range of plus or minus ten percent above and below the value of the stated item, parameter or term.

"Administration", or "to administer" means the step of giving (i.e. administering) a pharmaceutical composition to a subject. The pharmaceutical compositions disclosed herein are "locally administered". Systemic (i.e. intravenous or oral) routes of administration are excluded from the scope of the present invention, to the extent that a systemic administration would result in systemic effects of a systemically administered active ingredient. Systemic administration of a targeted active ingredient which does not result in systemic effects is not excluded from the scope of the present invention. Local administration includes, but is not limited to, intramuscular (i.m.) administration, intradermal administration, subcutaneous administration, intrathecal administration, intraperitoneal (i.p.) administration, topical contact, and implantation of a slow-release device such as polymeric implant or miniosmotic pump.

"Amino acid" includes polyamino acids.

"Animal protein free" means the absence of blood derived, blood pooled and other animal derived products or compounds. "Animal" means a mammal (such as a human), bird, reptile, fish, insect, spider or other animal species. "Animal" excludes microorganisms, such as bacteria. Thus, an animal protein free pharmaceutical composition can include a Clostridial neurotoxin. For example, an animal protein free pharmaceutical composition means a pharmaceutical composition which is either substantially free or essentially free or entirely free of a serum derived albumin, gelatin and other animal derived proteins, such as immunoglobulins. An example of an animal protein free pharmaceutical composition is a pharmaceutical composition which comprises or which consists of a botulinum toxin (as the active ingredient) and a recombinantly made albumin or other recombinantly made stabilizer or excipient.

"Botulinum toxin" means a neurotoxin produced by *Clostridium botulinum*, as well as a botulinum toxin (or the light chain or the heavy chain thereof) made recombinantly by a non-Clostridial species. The phrase "botulinum toxin", as used herein, encompasses the botulinum toxin serotypes A, B, C, D, E, F and G. Botulinum toxin, as used herein, also encompasses both a botulinum toxin complex (i.e. the 300, 600 and 900 kDa complexes) as well as the purified botulinum toxin (i.e. about 150 kDa). "Purified botulinum toxin" is defined as a botulinum toxin that is isolated, or substantially isolated, from other proteins, including proteins that form a botulinum toxin complex. A purified botulinum toxin may be greater than 95% pure, and preferably is greater than 99% pure.

"Clostridial neurotoxin" means a neurotoxin produced from, or native to, a Clostridial bacterium, such as *Clostridium botulinum*, *Clostridium butyricum* or *Clostridium beratti*, as well as a Clostridial neurotoxin made recombinantly by a non-Clostridial species.

"Entirely free (i.e. "consisting of" terminology) means that within the detection range of the instrument or process being used, the substance cannot be detected or its presence cannot be confirmed.

"Essentially free" (or "consisting essentially of") means that only trace amounts of the substance can be detected.

"Fragment" means a part of a larger native or recombinantly made protein. "Low molecular weight" fragment means a protein with a molecular weight of about 100 kDa or less.

"Modified botulinum toxin" means a botulinum toxin that has had at least one of its amino acids deleted, modified, or replaced, as compared to a native botulinum toxin. Additionally, the modified botulinum toxin can be a recombinantly produced neurotoxin, or a derivative or fragment of a recombinantly made neurotoxin. A modified botulinum toxin retains at least one biological activity of the native botulinum toxin, such as, the ability to bind to a botulinum toxin receptor, or the ability to inhibit neurotransmitter release from a neuron. One example of a modified botulinum toxin is a botulinum toxin that has a light chain from one botulinum toxin serotype (such as serotype A), and a heavy chain from a different botulinum toxin serotype (such as serotype B). Another example of a modified botulinum toxin is a botulinum toxin coupled to a neurotransmitter, such as substance P.

"Pharmaceutical composition" means a formulation in which an active ingredient can be a Clostridial toxin, such as a botulinum neurotoxin. The word "formulation" means that there is at least one additional ingredient in the pharmaceutical composition besides the biologically active ingredient. A pharmaceutical composition is therefore a formulation which is suitable for diagnostic or therapeutic administration (i.e. by intramuscular or subcutaneous injection or by insertion of a depot or implant) to a subject, such as a human patient. The pharmaceutical composition can be: in a lyophilized or vacuum dried condition; a solution formed after reconstitution of the lyophilized or vacuum dried pharmaceutical composition with saline or water, or; as a solution which does not require reconstitution. The active ingredient can be one of the botulinum toxin serotypes A, B, $C_1$, D, E, F or G or a tetanus toxin, all of which can be made natively by Clostridial bacteria. As stated, a pharmaceutical composition can be liquid or solid, for example vacuum-dried. The constituent ingredients of a pharmaceutical composition can be included in a single composition (that is all the constituent ingredients, except for any required reconstitution fluid, are present at the time of initial compounding of the pharmaceutical composition) or as a two-component system, for example a vacuum-dried composition reconstituted with a diluent such as saline which diluent contains an ingredient not present in the initial compounding of the pharmaceutical composition. A two-component system provides the benefit of allowing incorporation of ingredients which are not sufficiently compatible for long-term shelf storage with the first component of the two component system. For example, the reconstitution vehicle or diluent may include a preservative which provides sufficient protection against microbial growth for the use period, for example one-week of refrigerated storage, but is not present during the two-year freezer storage period during which time it might degrade the toxin. Other ingredients, which may not be compatible with a Clostridial toxin or other ingredients for long periods of time, may be incorporated in this manner; that is, added in a second vehicle (i.e. in the reconstitution fluid) at the approximate time of use.

"Protein stabilizer" (or "primary stabilizer") is a chemical agent that assists to preserve or maintain the biological structure (i.e. the three dimensional conformation) and/or biological activity of a protein (such as a Clostridial neurotoxin, such as a botulinum toxin). A stabilizer can be a protein or a protein fragment. Examples of protein stabilizers include recombinant albumins, gelatins or collagens, and fragments thereof. As disclosed herein, the primary stabilizer can be a synthetic agent that would not produce an immunogenic response (or produces an attenuated immune response) in a subject receiving a composition containing the primary stabilizer. In other embodiments of the invention, the protein stabilizers may be proteins from the same species of animal that is being administered the protein. Additional stabilizers may also be included in a pharmaceutical composition. These additional or secondary stabilizers may be used alone or in combination with primary stabilizers, such as proteins and polysaccharides. Exemplary secondary stabilizers include, but are not limited to non-oxidizing amino acid derivatives (such as a tryptophan derivate, such as N-acetyl-tryptophan ("NAT")), caprylate (i.e. sodium caprylate), a polysorbate (i.e. P80), amino acids, and divalent metal cations such as zinc. A pharmaceutical composition can also include preservative agents such as benzyl alcohol, benzoic acid, phenol, parabens and sorbic acid. A "recombinant stabilizer" is a "primary stabilizer" made by recombinant means, such as for example, a recombinantly made albumin (such as a recombinantly made human serum albumin), collagen, gelatin or a cresol, such as an M-cresol.

"Stabilizing", "stabilizes", or "stabilization" mean that a pharmaceutical active ingredient ("PAI") retains at least 20% and up to 100% of its biological activity (which can be assessed as potency or as toxicity by an in vivo $LD_{50}$ or $ED_{50}$ measure) in the presence of a compound which is stabilizing, stabilizes or which provides stabilization to the PAI. For example, upon (1) preparation of serial dilutions from a bulk or stock solution, or (2) upon reconstitution with saline or water of a lyophilized, or vacuum dried botulinum toxin containing pharmaceutical composition which has been stored at or below about −2 degrees C. for between six months and four years, or (3) for an aqueous solution botulinum toxin containing pharmaceutical composition which has been stored at between about 2 degrees and about 8 degrees C. for from six months to four years, the botulinum toxin present in the reconstituted or aqueous solution pharmaceutical composition has (in the presence of a compound which is stabilizing, stabilizes or which provides stabilization to the PAI) greater than about 20% and up to about 100% of the potency or toxicity that the biologically active botulinum toxin had prior to being incorporated into the pharmaceutical composition.

"Substantially free" means present at a level of less than one percent by weight of the composition (such as a pharmaceutical composition), formulation or medium.

"Therapeutic formulation" means a formulation can be used to treat and thereby alleviate a disorder or a disease, such as a disorder or a disease characterized by hyperactivity (i.e. spasticity) of a peripheral muscle.

A pharmaceutical composition within the scope of my invention can comprise a Clostridial toxin, such as a botulinum toxin, and a recombinant stabilizer. A pharmaceutical composition within the scope of my invention can also consist essentially of a botulinum toxin, and a recombinant stabilizer. Additionally, pharmaceutical composition within the scope of my invention can consist of a botulinum toxin, and a recombinant stabilizer.

The botulinum toxin can be present as a botulinum toxin complex (i.e. as an approximately 300 to about 900 kiloDalton complex depending upon the particular botulinum toxin serotype) or the botulinum toxin can be is present as a pure or purified botulinum toxin (i.e. as the botulinum toxin molecule of about 150 kiloDaltons). Additionally, the recombinant stabilizer can be a recombinant albumin, a recombinant collagen, a recombinant gelatin or other recombinant primary stabilizer. The pharmaceutical composition can also comprise a secondary stabilizer, such as a metal (i.e. zinc) or NAT.

Potency and relative potencies can be determined by a method used to determine a biological activity of a botulinum toxin, such as a mouse $LD_{50}$ assay. Generally, greater potency means that a lesser amount (i.e. fewer units) of a botulinum toxin pharmaceutical composition is required to paralyze a muscle. Preferably, a first botulinum toxin pharmaceutical composition has at least a 5% greater potency (and as much as a 40% greater potency) than does a second botulinum toxin pharmaceutical composition.

Another preferred embodiment of my invention is a pharmaceutical composition which can comprise (or which can consist essentially of or which can consist of) a botulinum toxin, a primary stabilizer, and a secondary stabilizer. The primary stabilizer can be a recombinant stabilizer (such as a r-G fragment) and the secondary stabilizer can be a metal, such as zinc. Other suitable secondary stabilizers can include caprylate (octanoate) and NAT.

The pharmaceutical composition is suitable for administration to a human patent to achieve a therapeutic effect, and the neurotoxin can be one of the botulinum toxin serotypes A, B, $C_1$, D, E, F and G. In a preferred embodiment of the present invention, the pharmaceutical composition comprises a botulinum toxin, and a rG fragment.

Whether the pharmaceutical composition comprises, beside the neurotoxin active ingredient, only a rG stabilizer or additional acid stabilizers, the pharmaceutical composition can retains its potency substantially unchanged for six month, one year, two year, three year and/or four year periods when stored at a temperature between about −1° C. and about −15° C.

Additionally, the indicated pharmaceutical compositions can have a potency or % recovery of between about 20% and about 100% upon reconstitution. Alternately or in addition, the pharmaceutical composition can have a potency of between about 10 U/mg and about 30 U/mg upon reconstitution, such as a potency of about 20 U/mg upon reconstitution. Significantly, the pharmaceutical composition is devoid of any albumin. Thus, the pharmaceutical composition can be substantially free of any non-toxin complex proteins. Notably, the amino acid can be present in an amount of between about 0.5 mg and about 1.5 mg of amino acid per 100 units of botulinum toxin.

The present invention also encompasses a lyophilized or vacuum dried pharmaceutical composition consisting essentially of a rG fragment and a botulinum toxin, wherein the botulinum toxin is stabilized by the high molecular weight polysaccharide. The botulinum toxin can be selected from the group consisting of botulinum toxin types A, B, $C_1$, D, E, F and G.

The botulinum toxin may be any one of the seven serotypes of botulinum toxin, or a recombinantly synthesized botulinum toxin. The botulinum toxin may be administered as an acute treatment, or it may be administered chronically.

The foregoing methods may be practiced utilizing a composition that comprises a botulinum toxin type A. In other embodiments of the invention, the foregoing methods may be practiced with a composition that comprises botulinum toxin type B. In further embodiments of the invention, the methods may be practiced with a composition that comprises a plurality of botulinum toxin serotypes, such as botulinum toxin serotypes selected from the group consisting of botulinum toxin serotypes A, B, $C_1$, D, E, F and G. In certain embodiments of the invention, purified botulinum toxins may be used. In other embodiments, modified botulinum toxins may be used.

In yet additional embodiments of the invention, the compositions used in the foregoing methods may be administered intramuscularly to the patient. In other embodiments, the compositions may be administered subcutaneously and/or intrathecally.

The present invention encompasses a pharmaceutical composition comprising (or consisting of or consisting essentially of) a botulinum toxin and a recombinant made gelatin with a molecular weight between about 8 kD and about 100 kD. The technology for obtaining specific gelatin fragments from animal sources or by use of recombinant DNA techniques is known. Thus, techniques are known for inserting the DNA (a gene) from one type of organism to another. For example, the human gene for production of one or more particular gelatin fragments can be inserted into the DNA of a bacterial cell. The bacterial cell will then divide to produce many new bacterial cells, each with the gene for the human gelatin fragments faithfully replicated. The bacteria can then produce human gelatin that can be harvested, fragmented or further fragmented for use in the present invention. A gelatin fragment is a gelatin molecule with a molecular weight of between about 8 kDa and about 100 kDa.

The pharmaceutical composition of the present invention can comprise (or consist or consist essentially of) a botulinum toxin selected from the group consisting of botulinum toxins types A, B, C, D, E, and F. The botulinum toxin is present as a botulinum toxin complex or as a pure botulinum toxin. The success of botulinum toxin type A to treat a variety of clinical conditions has led to interest in other botulinum toxin serotypes. Thus, at least botulinum toxins types, A, B, E and F have been used clinically in humans. Additionally, pure (approx 150 kDa) botulinum toxin has been used to treat humans. See e.g. Kohl A., et al., *Comparison of the effect of botulinum toxin A (Botox (R)) with the highly-purified neurotoxin (NT 201) in the extensor digitorum brevis muscle test,* Mov Disord 2000;15(Suppl 3):165. Hence, a botulinum toxin pharmaceutical composition can be prepared using a pure (approx 150 kDa) botulinum toxin, as opposed to use of a botulinum toxin complex. The molecular weight of the botulinum toxin protein molecule, for all seven of the known botulinum toxin serotypes, is about 150 kD. The botulinum toxins are released by *Clostridial bacterium* as complexes comprising the 150 kD botulinum toxin protein molecule along with one or more associated non-toxin proteins. Thus, the botulinum toxin type A complex can be produced by Clostridial bacterium as 900 kD, 500 kD and 300 kD forms (approximate molecular weights). Botulinum toxin types B and C, are apparently produced as only a 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemagglutinin protein and one or more non-toxin and/or non-toxic nonhemagglutinin proteins. Thus, a botulinum toxin complex can comprise a botulinum toxin molecule (the neurotoxic component) and one or more non toxic, hemagluttinin proteins and/or non toxin, non hemagluttinin proteins (the later can be referred to as NTNH proteins) These two types of non-toxin proteins (which along with the botulinum toxin molecule can comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex. The toxin complexes can be dissociated into toxin protein and hemagglutinin proteins by treating the complex with red blood cells at pH 7.3. or by subjecting the complex to a separation process, such as column chromatography, in a suitable buffer at a pH of about 7-8. The botulinum toxin protein has a marked instability upon removal of the hemagglutinin protein. Both pure toxin and the various botulinum toxin complexes set forth above are useful in the present invention.

A pharmaceutical composition within the scope of the present invention can comprise (or consist or consist essentially of) a botulinum toxin type A and a recombinant gelatin fragment with a molecular weight between about 25 kD and about 100 kD. Additionally, a pharmaceutical composition within the scope of the present invention can comprise a botulinum toxin, and a recombinant gelatin (i.e. a recombinant gelatin fragment) with a molecular weight between about 25 kD and about 100 kD, wherein the botulinum toxin present in the pharmaceutical composition has a potency (that is a recovered potency) of between about 80% and about 120% of the theoretical maximum potency of the botulinum toxin. Recovered potency of the botulinum toxin means the potency of the botulinum toxin after a lyophilized or vacuum dried (i.e. powdered) botulinum toxin pharmaceutical composition has been reconstituted with saline or water. Theoretical maximum potency (or synonymously "theoretical potency" or "maximum potency") means the potency of the same aqueous botulinum toxin pharmaceutical composition before it has been lyophilized or vacuum dried to a solid, powder form.

The present invention also encompasses a pharmaceutical composition wherein the botulinum toxin present in the pharmaceutical composition has a potency of at least about 80% of the theoretical potency of the botulinum toxin. Additionally, the pharmaceutical composition within the scope of the present invention can comprise (or consist or consist essentially of) a botulinum toxin, a recombinant gelatin fragment with a molecular weight between about 8 kD and about 100 kD and a buffer to adjust and maintain pH. A buffer is a substance which by its presence in solution increases the amount of acid or alkali that must be added to cause unit change in pH. Buffers are useful for maintaining a relatively constant concentration of hydrogen ions, for example to maintain a pH within the physiological range. The pH of mammalian blood is maintained close to 7.38 by biological buffer systems. Suitable buffers within the scope of the present invention can include, for example, sodium citrate, potassium citrate, sodium acetate, boric acid, potassium phosphate, ammonium sulfate, EDTA, potassium phosphate, sodium bicarbonate, sodium carbonate, sodium chloride, sodium phosphate, Tris and Tris Tris hydrochloride buffers.

The present invention can also include a pharmaceutical composition which comprises ((or consists or consists essentially of) a botulinum toxin, and a plurality of recombinant gelatin fragments with molecular weights between about 8 kD and about 100 kD. The present invention can also include a pharmaceutical composition which comprises (or which consists or which consists essentially of) a botulinum toxin a recombinant gelatin fragment with a molecular weight between about 8 kD and about 100 kD, and a compound selected from the group consisting of a polysaccharide, a surfactant, an amino acid, a polymer, an antioxidant, an antimicrobial agent, and a preservative.

Suitable polysaccharides can include starches (such as hetastarch and dextran), hyaluronic acid, glycogen, polyribose, chondroitin, dermatan, keratan, heparin, alginate and derivatives, salts and esters thereof.

Suitable surfactants can include:
EDTA
Polysorbate, such as polysorbate 20
Trisodium Nitrilotriacetate
Trisodium N-Hydroxyethlenediaminetriacetate
Trisodium Ethylenediaminetetraacetate
Trisodium N-Hydroxyethylenediaminetriacetate
Ethylenediaminetetraacetic Acid
Pentasodium Diethylenediameinepentaacetate Disodium Ethylenediaminetetraacetate
Tetrasodium Ethylenediaminetetraacetate, Dihydrate
Trisodium Nitrilotriacetate Solution
Poly Oxyethylene Octadecylamine
Poly(Oxyethylene)1,3 Diaminopropane
Poly Oxyethylene Soya Amine
Bis(2-Hydroxyethyl)Soya Amine
Poly Oxyethylene Tallow Amine
Bis(2-Hydroxyethyl)Tallow Amine
Poly Oxyethylene Tallow Amine
Phenoxyethanol
Chloroxylenol
Isopropyl Myristate
Isopropyl Palmitate
Stearic Acid, N-Butyl Ester
Glycol Distearate
Propylene Glycol Isostearate
Propylene Glycol Dipelargonate
Glyceryl Stearate
Polyglyceryl-3 Diisostearate
PEG-400 Monooleate
PEG-4 Dilaurate
PEG-8 Distearate
PEG-40 Stearate
Oleic Acid
Lanolin
PPG-5 Lanolin Wax Glyceride
Lanolin Oil
Lanolin Alcohol
Cocamide MEA
Cetearyl Isononanoate
Ceteareth-20
Cetearyl Alcohol
PEG-40 Castor Oil
Cetearyl Alcohol
Cetearyl Glucoside
PEG-75 Lanolin
PEG Ether of Oleyl, Cetyl Alcohol
Ceteareth-12
Ceteareth-20
Ceteareth-30
PPG-1-PEG-9 Lauryl Glycol Ether
Aluminum Starch Octenylsuccinate
PEG-3 Distearate
Sodium Laureth Sulfate
Glycol Distearate
Laureth-4 (and) Cocamidopr
Sodium Laureth Sulfate
Glycol Distearate
Lauryl Glucoside
Octyldodecanol
Hexyldecanol
Alkyl Dimethyl Benzyl Ammonium Chloride
Didecyl Dimethyl Ammonium Chloride
Alkyl Dimethyl Benzyl Ammonium Chloride
PEG-10 Soy Sterol
PEG-16 Soy Sterol
PEG-25 Soy Sterol
PEG-5 Soy Sterol
Soybean (Glycine Soja)Sterol
Ammonium Lauroyl Sarcosinate
Cococyl Sarcosine
Sodium Cocoyl Sarcosinate
Lauroyl Sarcosine
Sodium Lauroyl Sarcosinate
Potassium Cocoyl Hydrolyzed
Myristyl Alcohol
Stearyl Alcohol
Behenyl Alcohol
Sodium Cetearyl Sulfate
Quaternium-60
Propylene Glycol
Cocamidopropyl Betaine
Glyceryl Monostearate
Isododecyloxypropyamine
Lauryl Glucoside
Decyl Glucoside
PEG-15 Cocopolyamine
Isodecyloxypropyl Dihydroxyethyl Methyl Ammonium Chloride
Trimethyl Stearyl Ammonium Chloride Suitable amino acids can include alanine, arginine, asparagine, aspartic acid, cysteine, glutamine, glutamic acid, glycine, histidine, isoleucine, leucine, lysine, methionine, phenylalanine, proline, serine, theronine, tryptophan, tyrosine and valine.

Suitable polymers can include, for example, a polyvinyl propylene (i.e. a PVP), a PEG, such as PEG 3350, a poloxamer, such as poloxamer 188, and a Kollidon, such as a Kollidon 17

The present invention also includes a pharmaceutical composition which comprises (or which consists or which consists essentially of) a botulinum toxin, and a gelatin fragment with a molecular weight between about 8 kD and about 100 kD, where the gelatin fragment is derived from a native or naturally made gelatin.

DESCRIPTION

The present invention is based upon the discovery that a stabilized botulinum toxin can be made with one or more particular low molecular weight gelatin fragments.

As set forth herein, I have discovered that a botulinum toxin containing pharmaceutical formulation can be made with a recombinant gelatin fragment ("rG" fragment) as a stabilizer for the botulinum toxin.

The botulinum toxin present in the botulinum toxin pharmaceutical composition can be a native, recombinant, hybrid, chimeric or modified botulinum toxin type A, B, C, D, E, F or G. Additionally, the botulinum toxin can be present in the botulinum toxin pharmaceutical composition as either a complex or as a pure botulinum toxin. A botulinum toxin complex comprises a botulinum toxin molecule (about 150 kDa) and one or more non-toxic haemagluttinin and/or non-toxic non-haemagluttinin proteins. The complex can have a molecular weight of, for example, 300, 600 or 900 kDa, with the amount in excess of 150 kDa being attributed to the non-toxic haemagluttinin and/or non-toxic non-haemagluttinin protein components of the complex. The 150 kDa botulinum toxin molecule is also referred to as the neurotoxic component and as pure botulinum toxin.

An excipient that can be present in a botulinum toxin pharmaceutical composition can be a protein such as a gelatin fragment, such as a human gelatin fragment or a recombinantly made gelatin fragment. Another excipient that can be present in a botulinum toxin pharmaceutical composition can be sodium chloride. I have discovered that certain gelatin fragments can be used as stabilizing excipients in a botulinum toxin pharmaceutical composition. It is known to use of sodium chloride and albumin as bulking agents in a botulinum toxin pharmaceutical composition. Albumin has been used as an excipient to stabilize the toxin during drying and to prevent the toxin from adhering to surfaces, such as the glass surfaces onto which the toxin can come into contact during manufacture and storage. See e.g., Rader R. A., *Botulinum toxin A*, in Ronald Rader, ed. *BIOPHARMA: Biopharmaceutical Products in the U.S. Market* Rockville, Md.: Biotechnology Information Institute; 2001:pp. 271-274 (332), and; Rader R. A., *Botulinum toxin B*, in Ronald Rader, ed. *BIOPHARMA: Biopharmaceutical Products in the U.S. Market* Rockville, Md.: Biotechnology Information Institute; 2001: pp. 274-276 (333).

In certain embodiments of the invention, the pharmaceutical compositions of the invention may comprise a plurality of botulinum toxin serotypes. In other words, the composition may include two or more different botulinum toxin serotypes. For example, a composition may include botulinum toxin serotypes A and B. In another embodiment, a composition may include botulinum toxin serotypes A and E. Using a combination of botulinum toxin serotypes will permit caregivers to customize the composition to achieve a desired effect based on the condition being treated. In an additional embodiment of the invention, the composition may comprise a modified botulinum toxin. The modified botulinum toxin will preferably inhibit the release of neurotransmitter from a neuron, but may have a greater or lower potency than the native botulinum toxin, or may have a greater or lower biological effect than the native botulinum toxin.

My invention also encompasses addition of a preservative, either in the diluent or formulation itself, to allow extended storage. A preferred preservative can be saline containing benzyl alcohol.

The lyophilized neurotoxin is reconstituted before administering the neurotoxin to a subject by adding water, saline, or any buffer solution to the lyophilized neurotoxin. In certain embodiments, sodium free buffers may be preferred to help reduce denaturation of the neurotoxin.

The pharmaceutical compositions of the invention can be administered using conventional modes of administration. In preferred embodiments of the invention, the compositions are administered intramuscularly or subcutaneously to the subject. In other embodiments, the compositions of the invention may be administered intrathecally. In addition, the compositions of the invention may be administered with one or more analgesic or anesthetic agents.

The most effective mode of administration and dosage regimen for the compositions of this invention depends upon the type, severity, and course of the condition being treated, the animal's health and response to treatment, and the judgment of the treating doctor. Accordingly, the methods and dosages of the compositions should be tailored to the individual subject.

By way of example, and not by way of limitation, it may be preferred to administer the composition of the invention intramuscularly to reduce muscle spasms associated with a specific condition.

Compositions containing other serotypes of botulinum toxin may contain different dosages of the botulinum toxin. For example, botulinum toxin type B may be provided in a composition at a greater dose than a composition containing botulinum toxin type A. In one embodiment of the invention, botulinum toxin type B may be administered in an amount between about 1 U/kg and 150 U/kg. Botulinum toxin type B may also be administered in amounts of up to 20,000 U (mouse units, as described above). In another embodiment of the invention, botulinum toxin types E or F may be administered at concentrations between about 0.1 U/kg and 150 U/kg. In addition, in compositions containing more than one type of botulinum toxin, each type of botulinum toxin can be provided in a relatively smaller dose than the dose typically used for a single botulinum toxin serotype. The combination of botulinum toxin serotypes may then provide a suitable degree and duration of paralysis without an increase in diffusion of the neurotoxins (e.g. see U.S. Pat. No. 6,087,327).

EXAMPLES

The following examples set forth specific embodiments of the present invention and are not intended to limit the scope of the invention.

In the Examples below the well known mouse lethal dose$_{50}$ assay (the "MLD50 assay") was used to determine the recovered potency of the various botulinum toxin formulation made, and of the reference botulinum toxin formulations. Recovered potency (which is synonymous with reconstitution potency or potency upon reconstitution) can be referred to simply as potency. The MLD50 assay provides a determination of the potency of a botulinum toxin in terms of its mouse 50% lethal dose or "LD50". Thus, one unit (U) of a botulinum toxin is defined as the amount of botulinum toxin which upon intraperitoneal injection kills 50% (i.e. a $LD_{50}$) of a group of female Swiss Weber mice weighing 17-22 grams each at the start of the assay. The MLD50 assay is a validated method for measuring the potency of a reconstituted botulinum toxin or of a reconstituted botulinum toxin formulation. Each mouse is held in a supine position with its head tilted down and is injected intraperitoneally into the lower right abdomen at an angle of about 30 degrees using a 25 to 27 gauge ⅜" to ⅝" needle with one of several serial dilutions of the botulinum toxin in normal saline. The death rates over the ensuing 72 hours for each dilution are recorded. A minimum of six dilutions at 1.33 dose intervals are prepared and typically ten animals are used in each dosage group (60 mice employed therefore). Two reference standard assays are carried out concurrently (additional 60 mice employed). The dilutions are prepared so that the most concentrated dilution produces a death rate of at least 80% of the mice injected, and the least concentration dilution produces a death rate no greater than 20% of the mice injected. There must be a minimum of four dilutions that fall within the monotone decreasing range of the death rates. The monotone decreasing range commences with a death rate of no less than 80%. Within the four or more monotone decreasing rates, the two largest and the two smallest rates must be decreasing (i.e. not equivalent). The dilution at which 50% of the mice die within the three day post injection observation period is defined as a dilution which comprises one unit (1 U) of the botulinum toxin. A refined MLD50 assay has been developed which uses fewer (five instead of six) dilutions at 1.15 dose intervals and fewer mice (six instead of ten) per dilution tested.

Example 1

Human Serum Albumin Botulinum Toxin Pharmaceutical Composition

A botulinum toxin type A complex can be obtained from a culture of the Hall strain of *Clostridium botulinum* grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is then re-dissolved in a solution containing saline and albumin and sterile filtered (0.2 microns) prior to vacuum-drying. The vacuum dried composition can be reconstituted with sterile, non-preserved saline prior to injection. Each vial of vacuum dried composition can contain about 100 units (U) of *Clostridium botulinum* toxin type A complex, 0.5 milligrams of human serum albumin and 0.9 milligrams of sodium chloride in a sterile, vacuum-dried form without a preservative (Formulation A).

Example 2

Botulinum Toxin Formulations Stabilized with Recombinant Gelatin Fragments

Experiments were carried out to formulate a botulinum toxin with one or more particular low molecular recombinant gelatin ("rG") fragments and it was discovered that various particular low molecular weight recombinant gelatin fragments can be used to stabilize a botulinum toxin. All rG fragments set forth in this Example were obtained from FibroGen, Inc, South San Francisco, Calif.

Eight different recombinant gelatin botulinum toxin formulations were prepared. Each formulation contained:

(1) 2.5 mg or 5 mg of one of the 8.5 kDa, 25 kDa, 50 kDa or 100 kDa recombinant gelatin fragments obtained from Fibrogen (eight possible formulations therefore);

(2) 150 units of botulinum toxin type A complex (obtained by anaerobic fermentation of the Hall stain of *Clostridium botulinum* followed by purification of the botulinum toxin released into the fermentation medium, as set forth in Schantz E. J. et al., *Properties and use of botulinum toxin and other microbial neurotoxins in medicine*, Microbiol Rev March 1992;56(1):80-99) in either citrate buffered or non-buffered sterile water for injection.

The three ingredients were gently mixed in a 10 ml uncoated glass vial and the eight formulations were then vacuum-dried to form a fine white powder. The vacuum dried botulinum toxin formulations were then reconstituted with normal saline. Potency of the sixteen different preparations (the eight different formulations reconstituted with one of the two different reconstitution liquids) was then determined using the refined MLD50 assay. Results are shown in Table 1, where 100% botulinum toxin potency is 150 units and the citrate buffer used was a sodium citrate buffer.

TABLE 1

Potency of Recombinant Gelatin Botulinum Formulations

| rG (mol wt) | rG (mg) | Buffer | Potency (%) |
|---|---|---|---|
| 8.5 | 2.5 | None | <39 |
| 8.5 | 5 | None | 52 |
| 8.5 | 5 | 10 mM citrate, pH 5.5 | 110 |
| 8.5 | 5 | 10 mM citrate, pH 6.5 | 103 |
| 25 | 2.5 | None | 76 |
| 25 | 5 | None | 77 |
| 25 | 5 | 10 mM citrate, pH 5.5 | 101 |
| 25 | 5 | 10 mM citrate, pH 6.5 | 115 |
| 50 | 2.5 | None | 89 |
| 50 | 5 | None | 121 |
| 50 | 5 | 10 mM citrate, pH 5.5 | 88 |
| 50 | 5 | 10 mM citrate, pH 6.5 | >115 |
| 100 | 2.5 | None | 61 |
| 100 | 5 | None | 67 |
| 100 | 5 | 10 mM citrate, pH 5.5 | 99 |
| 100 | 5 | 10 mM citrate, pH 6.5 | 96 |

As set forth in this Example it was discovered that:

(a) native gelatin (i.e. a collagen hydrolysate) is not required to stabilize a botulinum toxin;

(b) different particular low molecular weight gelatin fragments (molecular weights from about 8 kDa to about 100 kDa) can be used to effectively stabilize a botulinum toxin (i.e. high recovered potency of the botulinum toxin observed);

(c) an additional bulking agent or excipient such as dextran, albumin or sucrose is not required to provide a stabilized recombinant gelatin fragment botulinum toxin pharmaceutical composition;

(d) the data obtained shows that higher molecular weight recombinant gelatin fragments (i.e. 100 kDa) does not necessarily provide greater stability to the botulinum toxin in the formulation. The data also shows that conversely a lower molecular weight recombinant gelatin fragments (i.e. about 8 kDa) do not necessarily impart a lesser stability to the botulinum toxin in the formulation. This finding appears to be counterintuitive. Since it is known that native gelatin can be used to stabilize a botulinum toxin, it would be expected that the closer a gelatin fragment used to stabilize a botulinum toxin comes to the size of the large medium molecular weight native gelatin molecule, so would the recovered potency of the botulinum toxin concomitantly increase. But the data from this experiment showed, for example, that the 100 kDa recombinant gelatin botulinum toxin formulation was less stable than was the 25 kDa recombinant gelatin botulinum toxin formulation.

(e) increasing (as by doubling) the weight amount of the recombinant gelatin present does not necessarily provide a significantly greater stability to the botulinum toxin. Sometimes increasing the amount of the recombinant gelatin present in the botulinum toxin formulation increased the stability of the botulinum toxin formulation and sometimes it didn't, the results depending upon the particular recombinant gelatin used in the recombinant gelatin botulinum toxin formulation. This is also a counterintuitive finding.

(f) adding an acidic pH buffer to the reconstitution fluid increases the recovered potency of the botulinum toxin formulation, except with regard to the 50 kDa recombinant gelatin botulinum toxin formulation. The fact that use of the same buffer did not provide for increased stability of all of the recombinant gelatin botulinum toxin formulations, is yet another factor (at least the third) showing that it could not be predicted or postulated before hand, without actual experimental data, whether a particular recombinant gelatin botulinum toxin formulation reconstituted with a certain reconstitution fluid would have a high or low stability.

(g) particular low molecular weight gelatin fragments, with our without the presence of a buffer in the reconstitution fluid, can provide an enhanced potency to the botulinum toxin present in a recombinant gelatin fragment botulinum toxin formulation. By "enhanced potency" it is meant that the recombinant gelatin fragment botulinum toxin formulation has a recovered potency which is near to (i.e. 96%) or which exceeds (i.e. 121%) the theoretical maximum potency (100%), as determined by the refined MLD50 assay.

It can be hypothesized that selecting the appropriate recombinant gelatin fragment to use in a recombinant gelatin botulinum toxin formulation can permit control of parameters of the formulation such as rate of diffusion. For example, a recombinant gelatin botulinum toxin formulation made with a 8.5 kDa recombinant gelatin fragment can be expected to diffuse more quickly faster than would a recombinant gelatin botulinum toxin formulation made with a 100 kDa recombinant gelatin fragment, thereby making the 8.5 kDa recombinant gelatin fragment botulinum toxin formulation more suitable for therapeutic large muscle injection and the 100 kDa recombinant gelatin botulinum toxin formulation more suited for cosmetic injection into smaller muscles, such as those of the forehead. Potentially a combination of recombinant gelatin fragments present in a recombinant gelatin botulinum toxin formulation can provide a mixture or range of such diffusion attributes.

The recombinant gelatin botulinum toxin formulation can be liquid, solid, semi-solid, gel, emulsion, cream, emollient, dispersion, etc. A preferred embodiment can be lyophilized. The recombinant gelatin botulinum toxin formulation can also include other bulking agents, excipients or stabilizers such as a sugar, polyvinyl propylene (PVP) a starch such as dextran, an amino acid, a polyol, a glycol, such as a polyethylene glycol, an oil, a buffering agent and/or an antioxidant.

A botulinum toxin pharmaceutical composition can be formulated using more that one rG fragment, such as by using one or more of 8.5 kD, 25 kD and/or 100 kD rG fragments in the formulation. A botulinum toxin pharmaceutical composition can also be formulated using a recombinant collagen.

Example 3

Use of a Botulinum Toxin Pharmaceutical Composition

A 48 year old male is diagnosed with a spastic muscle condition, such as cervical dystonia. Between about $10^{-3}$ U/kg and about 35 U/kg of a gelatin fragment containing botulinum toxin type A pharmaceutical composition of Example 2 can be injected intramuscularly into the patient. Within 1-7 days the symptoms of the spastic muscle condition are alleviated and alleviation of the symptoms persists for at least from about 2 months to about 6 months.

A pharmaceutical composition according to the invention disclosed herein has many advantages, including the following:

1. the pharmaceutical composition can be prepared free of an animal derived product and therefore free of any blood product infectious element such as a prion.

2. the pharmaceutical composition has stability and high % recovery of toxin potency comparable to or superior to that achieved with currently available pharmaceutical compositions.

Various publications and/or references have been cited herein, the contents of which, in their entireties, are incorporated herein by reference.

Although the present invention has been described in detail with regard to certain preferred methods, other embodiments, versions, and modifications within the scope of the present invention are possible. For example, a wide variety of stabilizing recombinant gelatin fragments are within the scope of the present invention. Additionally, particular low molecular weight animal-derived gelatin fragments, for example those obtained from digesting animal gelatin are also within the scope of the present invention.

Accordingly, the spirit and scope of the following claims should not be limited to the descriptions of the preferred embodiments set forth above.

I claim:

1. A pharmaceutical composition, comprising:
   (a) a botulinum toxin type A having a theoretical potency, and;
   (b) a recombinantly made gelatin with a molecular weight between about 8 kD and about 100 kD, a buffer to adjust and maintain the pH between about 5.5 and about 6.5; and
   wherein the pharmaceutical composition has a recovered potency of at least about 85% of the theoretical potency upon reconstitution with an aqueous solution subsequent to lyophilizing or vacuum drying.

2. The pharmaceutical composition of claim 1, wherein the botulinum toxin is present as a botulinum toxin complex.

3. The pharmaceutical composition of claim 1, wherein the botulinum toxin is present as a pure botulinum toxin.

4. A pharmaceutical composition, comprising:
   (a) a botulinum toxin type A having a theoretical potency, and;
   (b) a recombinant gelatin fragment with a molecular weight between about 25 kD and about 100 kD, a buffer to adjust and maintain the pH between about 5.5 and about 6.5;
   wherein the pharmaceutical composition has a recovered potency of at least about 85% of the theoretical potency upon reconstitution with an aqueous solution subsequent to lyophilizing or vacuum drying.

5. A pharmaceutical composition comprising:
   (a) a botulinum toxin type A having a theoretical potency, and;
   (b) a recombinant gelatin with a molecular weight of between about 25 kD and about 100 kD, a buffer to adjust and maintain the pH between about 5.5 to about 6.5, wherein the pharmaceutical composition has a recovered potency of between about 80% and about 120% of the theoretical potency upon reconstitution with an aqueous solution subsequent to lyophilizing or vacuum drying.

6. A pharmaceutical composition, comprising:
   (a) a botulinum toxin type A having a theoretical potency;
   (b) a recombinant gelatin fragment with a molecular weight between about 8 kD and about 100 kD, and;
   (c) a buffer to adjust and maintain the pH,
   wherein the botulinum toxin present in the pharmaceutical composition has a recovered potency of at least about 80% of the theoretical potency upon reconstitution with an aqueous solution subsequent to lyophilizing or vacuum drying and wherein the pharmaceutical composition is free of animal-derived products.

7. A pharmaceutical composition, comprising:
   (a) a botulinum toxin type A having a theoretical potency, and;
   (b) at least one plurality of recombinant gelatin fragment selected from the group consisting of recombinant gelatin fragments of molecular weights about 8.5 kD, about 25 kD, and about 50 kD; and a buffer to adjust and maintain the pH to about 6.5;
   wherein the the pharmaceutical composition has a recovered potency of at least about 100% of the theoretical potency upon reconstitution with an aqueous solution subsequent to lyophilizing or vacuum drying.

* * * * *